(12) United States Patent
Knopfle et al.

(10) Patent No.: US 7,111,411 B2
(45) Date of Patent: Sep. 26, 2006

(54) SYSTEM AND DEVICE FOR MEASURING BONE SCREWS

(75) Inventors: Christian Knopfle, Donaueschingen (DE); Gregg Diamond, Charlotte, NC (US)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 0 days.

(21) Appl. No.: 10/759,458

(22) Filed: Jan. 16, 2004

(65) Prior Publication Data

US 2004/0176770 A1  Sep. 9, 2004

(30) Foreign Application Priority Data

Jan. 17, 2003 (DE) ................. 103 01 688

(51) Int. Cl.
*G01B 3/14* (2006.01)
(52) U.S. Cl. .................. 33/562; 33/679.1; 33/545; 33/549; 33/512; 33/199 R
(58) Field of Classification Search .......... 33/511, 33/512, 679.1, 545, 548, 549, 551, 555.1, 33/555.2, 555.3, 562, 563, 565, 199 R, 484, 33/485, 486
See application file for complete search history.

(56) References Cited

U.S. PATENT DOCUMENTS

| | | | | |
|---|---|---|---|---|
| 1,860,174 A | * | 5/1932 | Cronk | 33/563 |
| 2,728,145 A | * | 12/1955 | Holladay | 33/199 R |
| 2,981,005 A | * | 4/1961 | Moe | 33/679.1 |
| 3,209,463 A | * | 10/1965 | Schorr | 33/199 R |
| 3,230,628 A | | 1/1966 | Hite | |
| 4,032,008 A | * | 6/1977 | Vecchiarelli | 206/379 |
| 5,013,318 A | * | 5/1991 | Spranza, III | 33/512 |
| 5,180,388 A | * | 1/1993 | DiCarlo | 606/60 |
| 5,309,648 A | * | 5/1994 | Allard et al. | 33/511 |
| 5,335,421 A | * | 8/1994 | Jones, Jr. | 33/679.1 |
| 5,409,493 A | | 4/1995 | Greenberg | |
| 5,501,020 A | * | 3/1996 | Welt | 33/555.2 |
| 5,515,614 A | | 5/1996 | Wing | |
| 5,732,821 A | | 3/1998 | Stone et al. | |
| 5,845,774 A | * | 12/1998 | Hausknecht | 206/379 |
| 6,030,162 A | | 2/2000 | Huebner | |
| 6,802,817 B1 | * | 10/2004 | Baxter-Jones et al. | 33/512 |

FOREIGN PATENT DOCUMENTS

| | | |
|---|---|---|
| DE | 3807526 | 9/1989 |
| DE | 4122045 | 1/1993 |

* cited by examiner

*Primary Examiner*—Diego Gutierrez
*Assistant Examiner*—Travis Reis
(74) *Attorney, Agent, or Firm*—Howard & Howard Attorneys, P.C.

(57) ABSTRACT

A measuring device for bone screw types of different shaft diameters is described. This measuring device has multiple receiving grooves for bone screws in a surface or an area near the surface. In the area of each receiving groove a length measuring scale, which is associated with one or more of the different bone screw types, is arranged. Also, for each of the receiving grooves a limit stop to work with a received bone screw is provided. The receiving grooves and/or the associated limit stops have a selectivity with respect to the shaft diameter of the bone screw types which can be received in the individual receiving grooves.

11 Claims, 3 Drawing Sheets

SYSTEM AND DEVICE FOR MEASURING BONE SCREWS

TECHNICAL FIELD

The invention concerns a measuring device for bone screws to be used during a surgical operation. The invention also concerns a measuring system which includes this measuring device.

BACKGROUND OF THE INVENTION

In surgical operations, for instance in the middle face area, there is often the problem that bone plates must be fixed to bones or bone fragments using suitable bone screws. To fix a bone plate, the surgeon will usually first make a preliminary bore hole in the bone or bone fragment using a suitable drill, and then select a suitably dimensioned bone screw, which should be inserted into the preliminary bore hole to fix the bone plate.

The surgeon selects a suitable bone screw depending on the depth of the preliminary bore hole and the hole diameter of the bone plate to be fixed. As part of this selection, it is often necessary to check the geometrical dimensions of a particular bone screw. Otherwise, there is the danger of a wrongly dimensioned bone screw being screwed into the bone or bone fragment.

The dangers for the patient which are associated with screwing in a wrongly dimensioned bone screw are obvious. As well as the bone plate being insufficiently held, for instance by a too short bone screw, in the case of a too long bone screw there is the danger that the screw tip exits again from the bone or bone fragment.

The invention is based on the object of giving a multifunctional measuring device for bone screws and a measuring system which includes this measuring device.

SUMMARY OF THE INVENTION

This object is achieved according to the invention by a measuring device for bone screw types of different shaft diameters. This measuring device has multiple receiving grooves for bone screws in a surface or an area near (e.g. under) the surface. In the area of each of the receiving grooves, a length measuring scale, which is associated with one or more of the different bone screw types, is arranged. Also, for each of the receiving grooves, a limit stop to work (or cooperate) with a received bone screw is provided, and the receiving grooves and/or the associated limit stops have a selectivity with respect to the shaft diameter of the bone screws which can be received in the individual receiving grooves.

The measuring device according to the invention allows reliable length measurement of different bone screw types, particularly depending on their shaft diameter. Above all in the case of bone screw types with different transitions from the screw shaft to the screw head, it is often difficult to make a precise statement about the length. The measuring device according to the invention allows more reliable measurements, especially in such cases, and for this purpose it may have length measuring scales with differently chosen "zero points", depending on the associated selectivity.

The measuring device according to the invention can have, in addition to the receiving grooves, multiple openings with different opening cross-sections. Usefully, at least one opening is associated with each receiving groove. The opening cross-section of the at least one opening which is associated with a particular receiving groove can be adapted to the selectivity of the receiving groove and/or of the limit stop associated with it.

The openings can be in the form of through openings or blind holes, and are suitably used to determine the shaft diameter of a particular bone screw before a length measurement. To determine the shaft diameter, the bone screw is inserted into one or more openings, to determine the opening of which the cross-section just allows the bone screw to be inserted. From the cross-section of this opening, the shaft diameter of the bone screw can then be determined. The invention thus allows combined measurement of the screw length and shaft diameter.

The openings can be arranged at different places of the measuring device. It has been shown to be useful to arrange the openings in the surface in which the receiving grooves are formed. However, the openings can also be formed at other places of the measuring device, for instance in faces which run vertically to the surface.

The receiving grooves can be formed completely in the surface of the measuring device, i.e. in such a way that both ends of the receiving grooves are limited within the surface. However, it is also possible that the receiving grooves are open at one end. It is thus conceivable that the receiving grooves open into a face of the measuring device. In other words, the receiving grooves can be open in the direction towards one face of the measuring device. This face usefully runs essentially vertically to the surface in which, or in the area of which, the receiving grooves are formed.

Particularly if the receiving grooves in the area of one face of the measuring device are open, the limit stops can also be arranged in the area of the face, or formed by the face itself. Preferably, one or more of the limit stops is provided as part of an extension of an associated receiving groove.

The limit stops can be arranged at different positions in relation to the associated receiving grooves. In general, the position of a limit stop in relation to the receiving groove will depend on which part of the bone screw the limit stop will work with for a length measurement. For instance, the limit stops can work with the tip or the head of a bone screw. According to a preferred form of the invention, the limit stops are formed to work with an underside (which faces the screw shaft of a bone screw) of the screw head. This includes working with an (e.g. conical) transition from a cylindrical screw shaft to a screw head.

The above-mentioned selectivity of a receiving groove and/or limit stop with respect to the shaft diameter of a bone screw can be implemented in various ways. In the simplest case, the receiving grooves have different widths, i.e. different dimensions vertically to their axial extension. Bone screws with such a shaft diameter, which is greater than the width of the receiving groove, can then no longer be placed or inserted into a particular receiving groove. According to another variant, the selectivity can be defined by means of the limit stop which is associated with a particular receiving groove. Thus every limit stop can have, opposite each other, two limit areas, the distance of which from each other defines the selectivity in each case. For instance, in the case of a limit stop which works with an underside (which faces the screw shaft of a bone screw) of the screw head, it can immediately be seen that as the distance between the two limit areas of this limit stop increases, bone screws of greater shaft diameter can be received.

A bone screw can be received into a receiving groove in various ways. Inserting the bone screws into the receiving grooves laterally (in the case of a receiving groove with at least one open end), or from above, is thus conceivable. So that the bone screws can be inserted into the receiving grooves, their open angle range with reference to the surface of the measuring device should be greater than or equal to 180° with respect to an axis of symmetry which runs along the axial extension of the receiving grooves. On the other hand, if the open angle range is less than 180° and in particular less than about 90°, the bone screw must be inserted into the receiving groove via a free end of the receiving groove. For the angle data, it is assumed that the screw shaft diameter is not significantly less than the width of a receiving groove. Quite generally, and irrespective of the groove width, an open angle in the range between 20° and 240° has been shown to be useful.

In practice, forming the limit stops and receiving grooves as separate components has been shown to be useful. The limit stops are preferably removable and can be replaced.

A measuring system according to the invention includes, as well as the measuring device described above, multiple bone screw types. The various bone screw types can have differently formed or dimensioned transitions from the screw shaft to the screw head.

Preferably, the measuring system according to the invention also includes a bone drill, which can be inserted to different depths into a bone or bone fragment. Information about a current drilling depth can be attached to the bone drill, and corresponding information can be found on the measuring device. The information about the drilling depth can include a colour scale.

BRIEF DESCRIPTION OF THE DRAWINGS

Further advantages and versions of the invention are given in the following description of preferred embodiments and the figures.

DESCRIPTION OF PREFERRED EMBODIMENTS

Below, various embodiments of a measuring device according to the invention and of a measuring system according to the invention are described. The various embodiments differ above all in the form of the receiving grooves for the bone screws.

Figure 1:
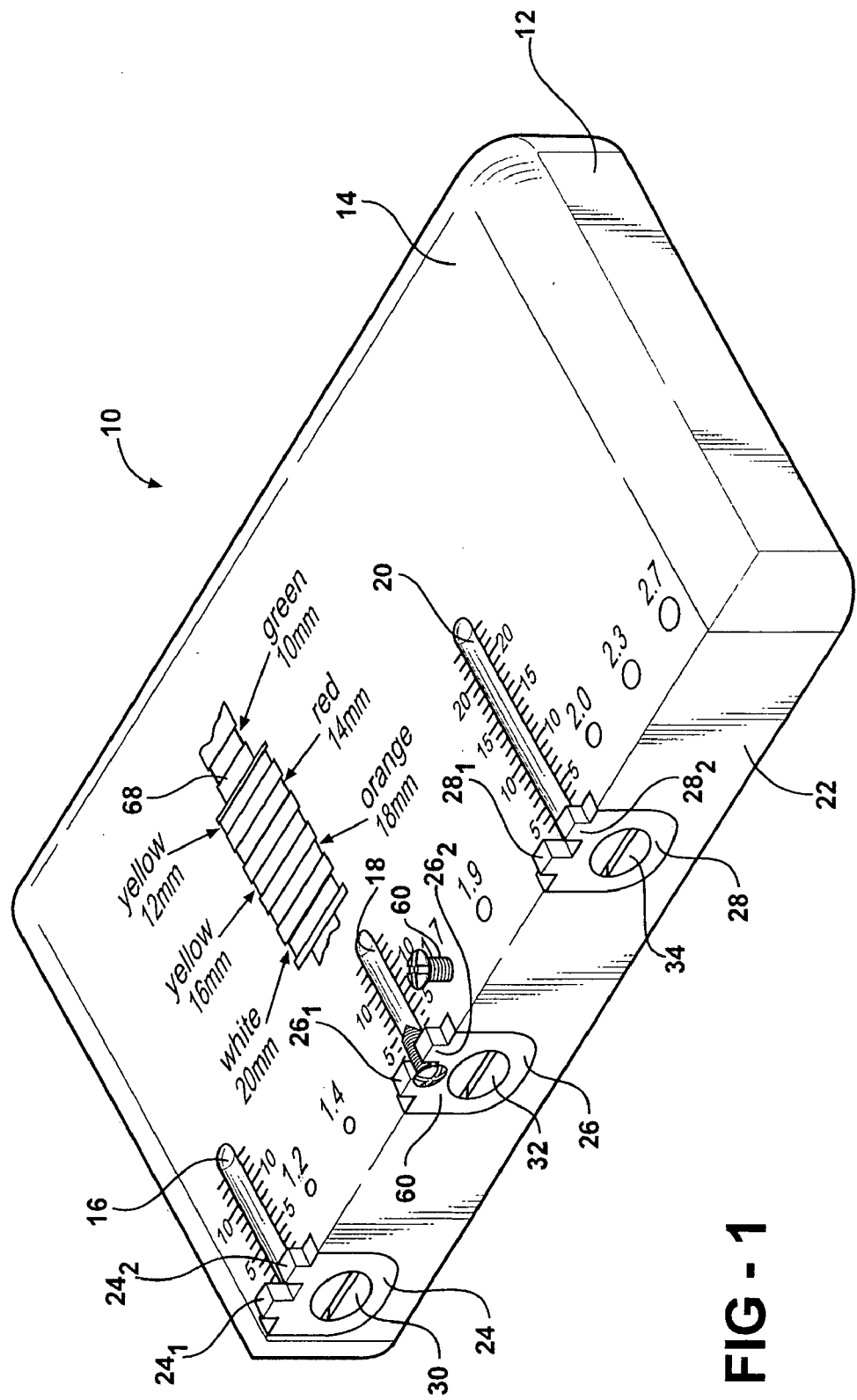
FIG. 1 shows a perspective view of a measuring device according to the invention.

FIG. 1 shows a perspective view of a first embodiment of a measuring device 10 according to the invention. The measuring device 10 includes a basic body 12 in the form of an aluminium block, which has, in one surface 14, multiple receiving grooves 16, 18, 20, which are formed by milling, for bone screws.

Each of the receiving grooves 16, 18, 20 opens into a limit stop 24, 26, 28 in the area of a face 22, which runs vertically to the surface 14, of the measuring device 10. The individual limit stops 24, 26, 28 are each fixed to the face 22 of the measuring device 10 by one fixing screw 30, 32, 34, so that they can be removed and replaced.

As shown in FIG. 1, the limit stops 24, 26, 28 are each in the form of an extension of the associated receiving grooves 16, 18, 20. More precisely, each of the limit stops 24, 26, 28 has two limiting elements $24_1$, $24_2$, $26_1$, $26_2$, $28_1$, $28_2$ which are arranged opposite and at a distance from each other, so that the receiving groove 16, 18, 20 can continue between two adjacent limiting elements $24_1$, $24_2$, $26_1$, $26_2$, $28_1$, $28_2$ in the direction towards the face 22. The limiting elements can also be in circular form.

Figure 2:
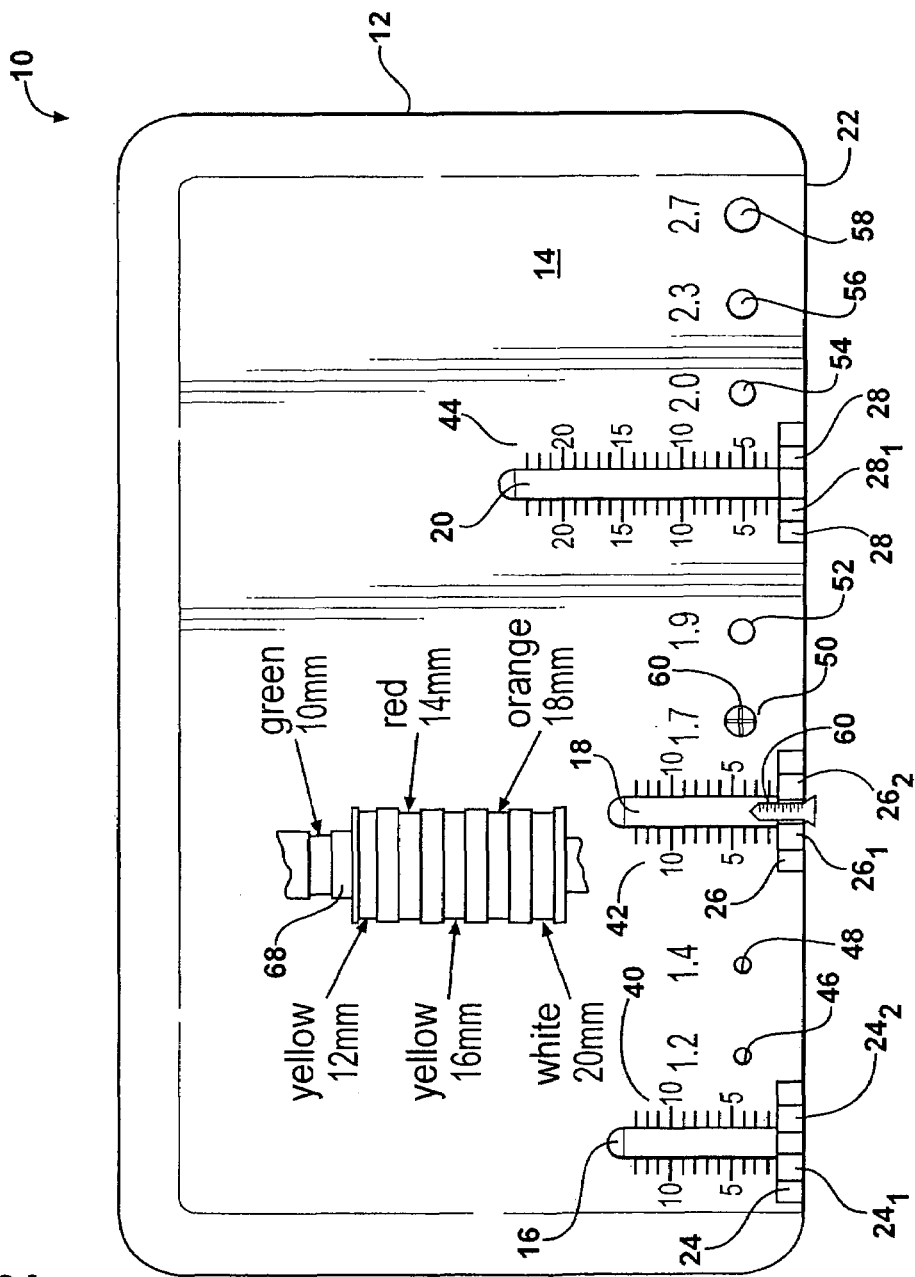
FIG. 2 shows an aspect of the measuring device according to FIG. 1.

FIG. 2 shows an aspect of the surface 14 of the measuring device 10 according to FIG. 1. It can be seen from FIG. 2 that a length measuring scale 40, 42, 44 is associated with each of the receiving grooves 16, 18, 20. The length measuring scales 40, 42, 44 are attached to the surface 14 on opposite sides of the receiving grooves 16, 18, 20. In principle, the length measuring scales could also be provided in the base of the receiving grooves 16, 18, 20.

The individual length measuring scales 40, 42, 44 have a differently chosen "zero point". This is to do with the fact that with different bone screw types with different transitions from screw shaft to screw head, the zero point for length measurement must be differently chosen. This subject is explained in more detail below.

As can also be seen from FIG. 2, multiple openings with different opening cross-sections are formed in the surface 14 of the measuring device 10. Thus two openings 46, 48 with opening cross-sections of 1.2 and 1.4 mm respectively are associated with the receiving groove 16. Two openings 50, 52 with opening cross-sections of 1.7 and 1.9 mm respectively are associated with the receiving groove 18, and three openings 54, 56, 58 with opening cross-sections of 2.0 mm, 2.3 mm and 2.7 mm respectively are associated with the receiving groove 20. In the example, the openings 46 to 58 are in the form of blind holes, and run vertically to the surface 14 of the measuring device 10.

The openings 46 to 58 are used to determine the shaft diameter of a particular bone screw. For this purpose, a bone screw is inserted into different openings from right to left in FIG. 2. In this way, the opening of which the opening cross-section just corresponds to the shaft diameter of the bone screw can be determined. The corresponding value of the shaft diameter can then be taken from writing (1.2, 1.4, 1.7, etc.) which is associated with each of the openings 46 to 58. What happens in practice, of course, is that the opening cross-section of each of the holes 46 to 58 is slightly greater than the diameter of the associated writing, so that, for instance, a bone screw with a shaft diameter of 1.4 mm can actually be inserted into the opening 48, which is labelled 1.4.

After the shaft diameter of a bone screw is determined in the way described above, to measure the length the bone screw is inserted into the receiving groove which is associated with the opening which was used to determine the cross-section. For instance, if it was determined, using the opening 56, that the shaft diameter of a bone screw to be measured is 2.3 mm, this bone screw is inserted into the receiving groove 20 which is associated with the opening 56.

As explained above, the length measuring scales 40, 42, 44 are associated with particular screw types. This means, for instance, that using the length measuring scale 42, which is associated with the receiving groove 18, to measure the length of a bone screw with a shaft diameter of 2.3 mm could give a wrong result. The danger of wrong measurement results is particularly great if the optional openings 46 to 58 are omitted in a modification of the measuring device 10 according to the invention.

To avoid wrong measurement results, i.e. the use of a wrong length measuring scale to determine the shaft length, every receiving groove/limit stop combination is equipped with selectivity with respect to the shaft diameter of the bone screws which can be received into the individual receiving grooves. This selectivity could be implemented, for instance, by using receiving grooves of different widths (see FIGS. 4 and 5). However, in the case of the embodiment which is now being described, the receiving grooves 16, 18, 20 have essentially the same width, and the desired selectivity is achieved by means of the individual limit stops 24, 26, 28. More precisely, the limiting elements $24_1$, $24_2$, $26_1$, $26_2$, $28_1$, $28_2$, which are provided in pairs, form the actual limit stop, and have a different distance from each other in each case, are used for this purpose.

Thus the two limiting elements $24_1$, $24_2$ of the limit stop 24 which is associated with the receiving groove 16 are at a distance of 1.5 mm from each other. This means that a bone screw with a shaft diameter of 1.5 mm and above cannot be measured in the receiving groove 16. The length measurement scale 40 is therefore calibrated with respect to length measurement of bone screws with shaft diameters of 1.2 mm or 1.4 mm (corresponding to the cross-sections of the openings 46, 48).

The distance between the two limiting elements $26_1$, $26_2$ of the limit stop 26 which is associated with the receiving groove 18 is 2.0 mm, and the limiting elements $28_1$, $28_2$ of the limit stop 28 which is associated with the receiving groove 20 are at a distance of 2.8 mm from each other. The calibration, i.e. particularly the position of the zero point in each case, of the length measurement scales 42 and 44 of the two receiving grooves 18 and 20 can therefore be adapted to length measurement of bone screws with particular shaft diameters.

Figure 3:
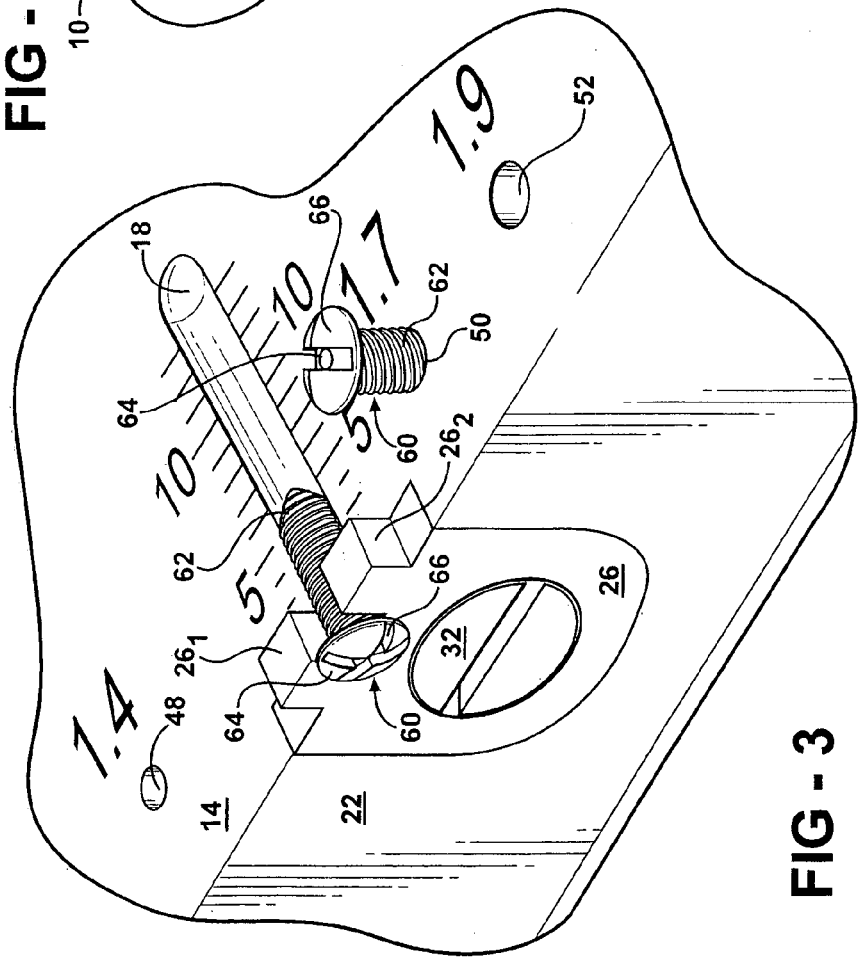
FIG. 3 shows an enlarged perspective view of a receiving groove of the measuring device shown in FIG. 1.

In FIGS. 2 and 3, measurement of a particular bone screw type is shown as an example. Each bone screw 60 of this type has a shaft 62 with a shaft diameter of 1.7 mm and a screw head 64. On the surface of the screw head 64 facing away from the screw shaft 62, a cross recess structure 66 is formed. The underside of the screw head 64 has a conical transition to the screw shaft 62. In FIGS. 2 and 3, it can clearly be seen that the limiting elements $26_1$, and $26_2$ of the limit stop 26 work with the conically formed underside of the screw head 64. In practice, particularly with bone screws with a conical transition from the screw shaft to the screw head, the measuring device 10 according to the invention has proved itself for exact determination of the length of bone screws with different shaft diameters.

In FIGS. 1 and 2, it can be seen that on the upper side 14 of the measuring device 10 a section of a bone drill according to the invention is represented. Only the shaft 68 of the bone drill is shown, not the drill tip. The shaft 68 of the bone drill, like the measuring device 10 itself (because of the labelled representation of the shaft 68 on the surface 14) is provided with information about an achieved drilling depth. In the example, this information consists, on the one hand, of a colour scale on the shaft 68 of the bone drill, and on the other hand of an assignment of colours and drilling depths on the surface 14 of the measuring device 10. Thus if a yellow colour ring on the shaft 68 of the bone drill can be detected during drilling, this corresponds to an achieved drilling depth of 12 mm, and if a white colour ring can be detected, this corresponds to an achieved drilling depth of 20 mm. Depending on the drilling depth, which can be read off from the representation on the surface 14, the surgeon can then decide what screw length is required, and verify the length of a provided bone screw using the measuring device 10 according to the invention, in the way explained above.

Figure 4:
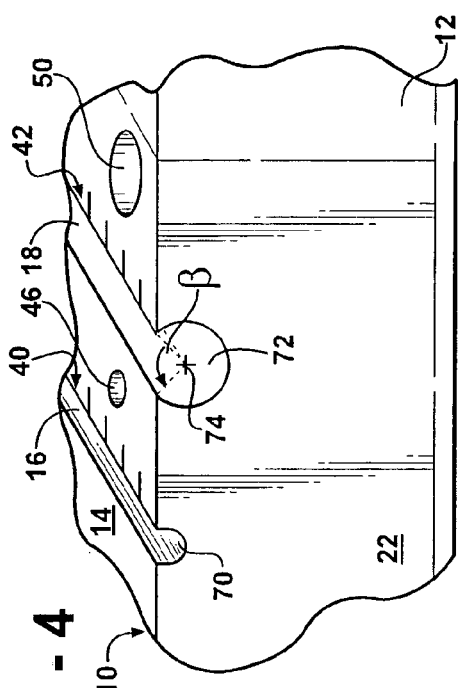
FIG. 4 shows a first alternative regarding the form of the receiving grooves.

In FIG. 4, a second embodiment of a measuring device 10 according to the invention is shown schematically. The measuring device according to the invention, in the second embodiment, is the same in many respects as the measuring device of the first embodiment, which is described with reference to FIGS. 1 to 3. For this reason, equivalent elements are given the same reference symbols, and a repeated description of these elements is omitted.

The measuring device 10 according to FIG. 4 has two receiving grooves 16, 18 of different widths (to achieve selectivity with respect to the shaft diameter) and two openings 46, 50 for measuring bone screws with a shaft diameter of either 1.2 mm or 1.7 mm. In contrast to the measuring device according to the first embodiment, in the case of the measuring device 10 according to the second embodiment which is shown in FIG. 4, the limit stops which are associated with the receiving grooves 16, 18 for the undersides of bone screw heads are formed from the face 22 itself. In other words, there are no removable or replaceable limit stops. This simplifies the production of the measuring device 10 according to the invention in the second embodiment.

Another difference is that the bone screws to be measured cannot be inserted from above into the receiving grooves 16, 18, but must be inserted with their tips forward into the open ends 70, 72 of the receiving grooves 16, 18. The reason for this is the fact that the receiving grooves 16, 18, with respect to an axis of symmetry which runs along their axial extension, have an open angle range of less than 180° with reference to the surface 14. For instance, if the receiving groove 18 is considered, this has an open angle β of approximately 100° with reference to the surface 14, with respect to an axis of symmetry 74 which runs along its axial extension.

Figure 5:
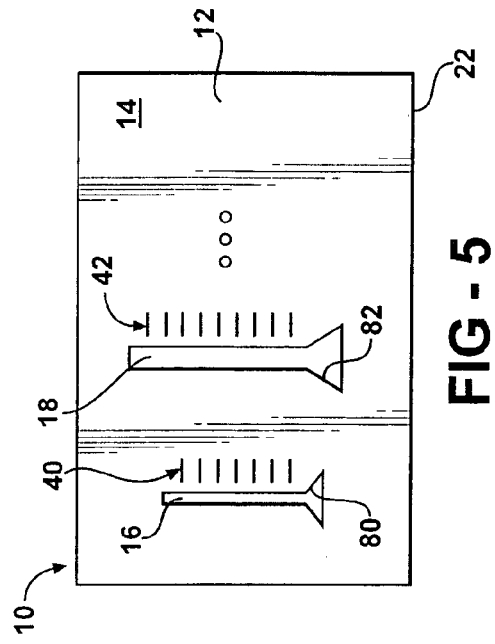
FIG. 5 shows a second alternative regarding the form of the receiving grooves.

In FIG. 5, a third embodiment of a measuring device 10 according to the invention is shown. Again, the reference symbols of the first embodiment, which was explained with reference to FIGS. 1 to 3, are used for equivalent elements.

In the third embodiment, which is shown in FIG. 5, the receiving grooves 16, 18 are formed completely in the surface 14 of the measuring device 10. Both ends of each of the receiving grooves 16, 18 are therefore limited. The limit stops 80, 82 to work with a conically formed underside of a bone screw head are also formed in the surface 14. As in the case of the second embodiment (FIG. 4), selectivity with respect to the shaft diameter is achieved by choosing different shaft widths. In the case of the embodiment which is shown in FIG. 5, the provision of additional openings to determine the shaft diameter is omitted.

The above-described embodiment of the invention is intended to be an example of the present invention, and alterations and modifications may be effected thereto, by those of ordinary skills in the art, without departing from the scope of the invention which is defined by the claims appended hereto.

The invention claimed is:

1. A measuring device for bone screws having different shaft diameters, comprising:
   a body having a surface and an edge with a face running essentially vertically to the surface at the edge;
   multiple receiving grooves defined in the surface for receiving the bone screws, each of the receiving grooves having an open end in the face of the body at the edge of the body;
   a length measuring scale defined at each of the receiving grooves for measuring the bone screws; and
   a limit stop associated with each of the receiving grooves for cooperating with a received bone screw, each limit stop including two limiting elements projecting upwardly from the surface and defining a channel between the two limiting elements extending downwardly below the surface, the two limiting elements having a spacing between each other that defines a selectivity with respect to the shaft diameter of the bone screw which can be measured in the associated receiving groove, wherein the limit stops are arranged in the region of the face at the edge of the body to form part of the face.

2. The measuring device according to claim 1, wherein the body defines multiple openings with different opening cross-sections, at least one opening being associated with each of the individual receiving grooves and the opening cross-section of the at least one opening which is associated with a particular receiving groove being adapted to the associated selectivity.

3. The measuring device according to claim 2, wherein the openings are arranged in the surface in which the receiving grooves are formed.

4. The measuring device according to claim 1, wherein the limit stops are formed to cooperate with undersides of screw heads.

5. The measuring device according to claim 1, wherein the receiving grooves have an open angle range between 20° and 240° with reference to the surface, with respect to an axis of symmetry which runs along their axial extension.

6. The measuring device according to claim 5, wherein the open angle range is less than approximately 175°.

7. A measuring system comprising:
a body having a surface and an edge with a face running essentially vertically to the surface at the edge;
multiple bone screws having different shaft diameters;
multiple receiving grooves defined in the surface for receiving the bone screws, each of the receiving grooves having an open end in the face of the body at the edge of the body;
a length measuring scale defined at each of the receiving grooves for measuring the bone screws; and
a limit stop associated with each of the receiving grooves to cooperate with a received bone screw, each limit stop including two limiting elements projecting upwardly from the surface and defining a channel between the two limiting elements extending downwardly below the surface, the two limiting elements having a spacing between each other that defines a selectivity with respect to the shaft diameter of the bone screw which can be measured in the associated receiving groove, wherein the limit stops are arranged in the region of the face at the edge of the body to form part of the face.

8. The measuring system according to claim 7, wherein the bone screws have differently dimensioned transitions from screw shaft to a screw head.

9. The measuring system according to claim 7, further including a bone drill, in such a form that is insertable to different depths into a bone or bone fragment.

10. The measuring system according to claim 9, wherein information about a current drilling depth is attached to the bone drill, and corresponding information is provided on to the measuring device.

11. The measuring system according to claim 10, wherein the information about the drilling depth includes a color scale.

* * * * *